US006770619B2

(12) United States Patent
Larsson et al.

(10) Patent No.: US 6,770,619 B2
(45) Date of Patent: Aug. 3, 2004

(54) LUNG SURFACTANT COMPOSITIONS WITH DYNAMIC SWELLING BEHAVIOR

(76) Inventors: Marcus Larsson, Norra Vallgatan 4 S-223 62, Lund (SE); Kåre Larsson, Norra Villavägen 7B S-237 34, Bjärred (SE); Per Wollmer, Brännmästarevägen 12 S-232 53, Åkarp (SE); Burkhard Lachmann, Wittenbrem 27 NL-3068 TL, Rotterdam (NL); Johannes Jacobus Haitsma, Merellaan 645 NL-3145 GA, Massluis (NL)

( * ) Notice: Subject to any disclaimer, the term of this patent is extended or adjusted under 35 U.S.C. 154(b) by 0 days.

(21) Appl. No.: 09/945,242

(22) Filed: Aug. 31, 2001

(65) Prior Publication Data

US 2002/0072540 A1 Jun. 13, 2002

(30) Foreign Application Priority Data

Sep. 1, 2000 (DK) ........................................ 2000 01301

(51) Int. Cl.[7] .................... C07K 14/785; C07K 14/435; A61K 9/14; A61K 47/42

(52) U.S. Cl. ........................... 514/2; 514/773; 514/826; 514/975; 424/557; 424/489; 424/459; 424/434

(58) Field of Search ............................ 514/2, 773, 826, 514/975; 424/557, 489, 459, 434

(56) References Cited

U.S. PATENT DOCUMENTS 6,129,934 A * 10/2000 Egan et al. ................. 424/557

FOREIGN PATENT DOCUMENTS

| | | | |
|---|---|---|---|
| EP | 0 413 957 A2 | 2/1991 | ............ C07K/7/08 |
| EP | 0 553 410 A1 | 3/1993 | ......... A61K/31/685 |
| EP | 0 335 133 A2 | 4/1998 | .......... A61K/47/00 |
| WO | PCT/IB01/01609 | 8/2001 | |

OTHER PUBLICATIONS

Takahashi et al., Biophysical Properties of Protein–Free, Totally Synthetic Pulmonary Surfactants, ALEC and Exosurf, in comparison with surfactant TA. Acta Paediatr Jpn Dec. 1994; 36(6): 613–8 see: abstract.*

E.G. Bligh and W.J. Dyer, "A Rapid Method of Total Lipid Extraction and Purification", Canadian Journal of Biochemistry and Physiology vol. 37, No. 8, Aug., 1959 (7 pages).

J. Chu, M.D.; J.A. Clements, MD.; E.K. Cotton, M.D.; M.H. Klaus, M.D.; A.Y. Sweet, M.D.; W.H. Tooley, M.D.; "Neonatal Pulmonary Eischemia" Pediatrics, Vol 40, No. 4, Part II, Oct. 1967 (73 aaages total).

G.C. Liggins, M,B., Ph.D., F.R.C.O.G.; and R.N.Howie, M.B., Ph.D., M.R.A.C.P. "A Controlled Trial of Antepartum Glucocorticoid Treatment for Prevention of the Respiratory Distress Syndrome in Premature Infants", Pediatrics, vol. 50, No. 4, Oct. 1972 (10 pages).

Hallman, M., Bry; K. Hoppu, K., Lappi, M., Pohjavouri., M., "Insotol Supplementation in Prematrue Infants with Respiratory Distress Syndrome", The New England Journal of Medicine, vol. 326, No. 19, May, 1992.

Yao, L. Richardson, C, Ford, C., Mathialagan, N., Mackie, G., Hammond, G.L., Haarding, P.G.R., Possmayer, Expression of Mature Pulmonary Surfactant–Associated Protein B (SP–B) in *Escherichia coli*, Using Truncated Human SP–B cDNAs, Biochemistry and Cell Biology, vol. 68, 1990.

* cited by examiner

*Primary Examiner*—Frederick Krass
*Assistant Examiner*—Clinton Ostrup
(74) *Attorney, Agent, or Firm*—Peter F. Corless; Edwards & Angell, LLP

(57) ABSTRACT

Lung surfactant compositions are provided which can form a swelling phase when dispersed in a medium containing electrolytes. Hereby, a more active spreading of the lung surfactant into the alveoli can be obtained after administration to the lungs. Further provided are a pharmaceutical composition and a pharmaceutical kit comprising a lung surfactant composition as well as to a method for the treatment, prevention and/or diagnosis of respiratory distress syndrome or other pulmonary diseases that are associated with a deficiency of a lung surfactant.

74 Claims, 4 Drawing Sheets

LUNG SURFACTANT COMPOSITIONS WITH DYNAMIC SWELLING BEHAVIOR

FIELD OF THE INVENTION

The present invention relates to lung surfactant compositions which are capable of forming a dynamic swelling phase when dispersed in a medium containing electrolytes. The dynamic swelling process can be observed by polarising microscopy and results in formation of a birefringent network or tubules at an air/liquid interface. The dynamic swelling process results in a spreading of the lung surfactant over an increased surface area compared to the spreading of the lung surfactant in a non-dynamic swelling phase. The spreading takes place during a specific span of time after dispersion of a lung surfactant in e.g. a physiological electrolyte solution. Hereby, a more active spreading of the lung surfactant into the alveoli can be obtained after administration to the lungs, which in turn opens the possibility to use such a composition as a carrier for therapeutically, prophylactically and/or diagnostically active substances into the lungs or other organs or body areas that are hard to access.

The invention also relates to a pharmaceutical composition and a pharmaceutical kit comprising a lung surfactant composition as well as to a method for the treatment, prevention and/or diagnose of respiratory distress syndrome (IRDS or ARDS) or other pulmonary diseases that are associated with a deficiency of a lung surfactant.

BACKGROUND OF THE INVENTION

Lung surfactants (LS) are complex and highly surface-active materials composed of lipids and proteins that are found in the fluid lining the alveolar surface of the lungs. Their principal property is to reduce the surface tension in the lungs, which is achieved through the presence of the lipids as an organised structure at the air-liquid interface in the alveoli. LS prevents alveolar collapse at low lung volumes and decreases the work of breathing during normal and forced respiration (biophysical functions). In addition, it is involved in the protection of the lungs from injuries and infections caused by inhaled particles and microorganisms (immunological, non-biophysical functions). LS is synthesised and secreted by alveolar type II cells. (For a review, see Robertson and Taeusch, 1995.)

The constitution of a lung surfactant may vary with various factors such as species, age, and general health conditions of the subject. Various natural and synthetic constituents can substitute for each other in a surfactant. Therefore, even a non-rigorous definition of what the lung surfactant is and what should be included in a lung surfactant for therapeutic use is dependent on the situation. Surfactants isolated from lung lavage of healthy mammals contain about 10% protein (half of which is surfactant specific), and about 90% lipids, of which about 80% are phospholipids and about 20% are neutral lipids, including about 10% unesterified cholesterol. The phospholipid fraction contains mostly (about 76%) phosphatidylcholine (PC), about two thirds is dipalmitoyl phosphatidylcholine (DPPC), and the rest is unsaturated. About 11% of the phospholipids are made up of phosphatidylglycerol (PG), about 4% phosphatidylinositol, about 3% phosphatidylethanolamine, about 2% phosphatidylserine, about 1.5% sphingomyelin and about 0.2% lysophosphatidylcholine. Surfactant protein A (SP-A) represents 4% of surfactant and SP-B and SP-C and SP-D each make up less than 1%, according to current estimates.

SP-A and SP-D belong to the collectin subgroup of the G-type lectin superfamily. SP-A binds dipalmitoyl phosphatidylcholine and SP-D binds phosphatidylinositol. SP-A also interacts with alveolar type II cells, implicating SP-A in surfactant phospholipid homeostasis. SP-A is required for the formation of tubular myelin from secreted lamellar body material.

Surfactant deficiency remains the most common and serious pulmonary affliction of premature infants. Surfactant deficiency is the major factor responsible for respiratory distress syndrome of the newborn (IRDS) and for adult respiratory distress syndrome (ARDS). Since the 1960's, the exogenous administration of lung surfactant for the treatment of these syndromes has been studied.

A pathophysiologic role for surfactant was first appreciated in premature infants with respiratory distress syndrome (IRDS) and hyaline membrane disease Use of exogenous lung surfactant and corticosteroid administration has made a major impact on improving survival and reducing morbidity in this disease with consequent alterations in the clinical and radiographic course.

Initial attempts at improving the treatment of RDS with lung surfactant replacement during the 1960's (Chu et al., 1967) failed, largely because of a lack of knowledge about lung surfactant compositions and distributions. Liggins and colleagues (Liggins et al., 1972) were the first to utilise corticosteroids for the enhancement of foetal lung maturation, thereby reducing the risks and complications of RDS after birth. It is feasible that combining corticosteroids with thyroid-releasing hormone will enhance prenatal prophylaxis for RDS, and also inositol can be given as a substrate for lung surfactant production to infants in the early course of RDS.

A number of approaches for the design and the use of lung surfactant replacement for RDS have also been tried. The most straightforward approach is to replace with human lung surfactant. Human pulmonary lung surfactant can only be harvested by lavage procedures, though, which may disrupt its preexisting biophysical and biochemical microorganisation. As seen in a study by Hallman and co-workers, (Hallman et al., 1983), such a preparation was successful in clinical trials, but because of the difficulties in obtaining large quantities of human lung surfactant, it is not in commercial production.

These limitations make the production of synthetic lung surfactant desirable A second approach is therefore to learn the functions of the various lung surfactant constituents and then construct lung surfactants that might be more easily obtained or less expensive than the isolation of the natural products.

Exosurf is a commercially available preparation containing DPPC, hexadecanol and tyloxapol. Hexadecanol and tyloxapol mimic, to some degree, the functions of surfactant proteins, PG and other lipids in natural lung surfactant. Several groups have added surfactant proteins to lipids, designing the proteins to mimic structure and function of native surfactant proteins.

Furthermore, there are new strategies that add surfactant proteins to lipid mixtures that include formulating proteins using de novo peptide synthesis or recombinant DNA techniques (Yao et al., 1990)

An ideal therapeutic lung surfactant should share many of the attributes of any ideal therapy. It should be stable, readily available, easy to make, inexpensive and have an easy route of administration, a half-life consonant with the disease process, and fully understood mechanisms of action, metabolism and catabolism. It should have maximum efficacy for the disease without toxicity, intolerance, immunogenicity or side effects. It should mimic the effects of the natural lung surfactant, improve the gas exchange in the lungs, improve lung mechanics, improve functional residual capacity, resist inactivation, display optimal distribution characteristics, and have a known clearance mechanism. Its use should completely reverse the primary disease process and repair or allow the body to repair secondary damage from the primary disease.

Available therapeutic lung surfactants are of two types: those that are prepared from mammalian lungs and those made from synthetic compounds. Bovine and porcine surfactants contain SP-8 and SP-C, associated with phospholipids, but SP-A and SP-D are only present in the whole natural surfactant. Examples of synthetic lung surfactants that are commercially available at present are Exosurf and ALEC.

The commercially available lung surfactants are mostly presented as ready-mixed liquids, but Exosurf and Alveofact are supplied as a lyophilised powder that has to be reconstituted with saline before use.

Surfactant therapy is at present an established part of routine clinical management of newborn infants with IRDS. An initial dose of about 100 mg/kg is usually needed to compensate for the deficiency of alveolar surfactant (lung surfactant) in these babies, and repeated treatment is required in many cases. Recent experimental and clinical data indicate that large doses of exogenous lung surfactant may be beneficial also in conditions characterised by inactivation of lung surfactant, caused by, for example, aspiration of meconium, infection, or disturbed alveolar permeability with leakage of plasma proteins into air spaces.

The acute response to lung surfactant therapy depends on the quality of the exogenous material (modified natural lung surfactant is generally more effective than protein-free synthetic surfactants), timing of treatment in relation to the clinical course (treatment at an early state of the disease is better than later treatment and may reduce the subsequent need for mechanical ventilation) and mode of delivery (rapid instillation via a tracheal tube leads to a more uniform distribution and is more effective than slow airway infusion). Treatment with aerosolised surfactant improves lung function in animal models of surfactant deficiency, but is usually associated with large loss of the nebulised material in the delivery system. Furthermore, data from experiments on immature newborn lambs indicate that treatment response may depend on the mode of resuscitation at birth, and that manual ventilation with just a few large breaths may compromise the effect of subsequent surfactant therapy. The widespread clinical use of lung surfactant has reduced neonatal mortality and lowered costs for intensive care in developed countries.

The most efficient lung surfactants at present are prepared from mammalian lungs. The yield is very low and the therapy is therefore very expensive. Therefore there is an urgent need to improve their efficiency and to standardise their application.

SUMMARY OF THE INVENTION

The present invention provides a lung surfactant composition comprising a lung surfactant, which—when dispersed as powder or particles in 0.9% w/w sodium chloride in a concentration of 10% w/w at ambient temperature—is capable of forming, in the course of swelling, a birefringent network or tubules at an air-liquid-solid interface within a time period of from about 0.5 to abut 120 min such as, e.g. from about 3 to about 60 min as observed by polarising microscopy.

The birefringent network or tubules are formed during a dynamic swelling process that takes place in the span of time from the lung surfactant is dispersed in a medium containing electrolytes and to the steady-state of swelling is reached (i.e. at equilibrium).

Thus, in another aspect the invention relates to a lung surfactant composition, which—when dispersed as a powder or as particles in an electrolyte solution having an ionic strength of at least about 5 mM such as, e.g., at least about 10 mM, at least about 15 mM, at least about 20 mM, at least about 25 mM, at least about 50 mM, at least about 75 mM, at least about 100 mM or at least about 125 mM or at an ionic strength corresponding to physiological conditions, and the thus obtained dispersion has a concentration of water of at least about 55% w/w such as, e.g. at least about 60%, at least about 65%, at least about 70%, at least about 75%, at least about 80%, at least about 85%, at least about 90%, at least about 95% or at least about 98% w/w,—is subject to a dynamic swelling process during which a birefringent network or tubules are formed, as observed by polarising microscopy, and the dynamic swelling process ends when steady-state is reached.

When dispersed in an electrolyte solution a liquid crystalline lamellar phase of the phospholipids is formed. The lipid-protein bilayer structure has been found to be organising towards an active establishment of an equilibrium composition, which is microscopically perceptible as a formation of a birefringent complex network. A LS composition for administration e.g. at a predetermined time point or during a well-defined time period is provided as well as means for determining said optimal time point or time period for a lung surfactant composition.

A more active spreading of a lung surfactant into the alveoli can be obtained when applying to the lungs or other parts of the respiratory system a lung surfactant that has dynamic swelling behaviour in a medium containing electrolytes. In this manner an improved treatment, prevention or diagnosis can be obtained.

Furthermore, a lung surfactant composition according to the invention may be used as a carrier for therapeutically, prophylactically and/or diagnostically active substances e.g. for pulmonary drug delivery.

The invention also provides a pharmaceutical composition, a pharmaceutical kit and method for an improved treatment of respiratory distress syndrome (RDS) or other respiratory or pulmonary diseases that may be associated with deficiency of surfactant.

In a still further aspect the invention provides an in vitro validation method for testing individual batches of a lung surfactant composition which has dynamic swelling behaviour when dispersed in an electrolyte solution, the method comprising a) determining $t_{1/2}$ for maximum dynamic swelling as described herein, b) comparing the thus obtained $t_{1/2}$ with a in vivo—in vitro correlation curve, obtained as described herein, and c) evaluating the batch as acceptable or not acceptable.

The invention also relates to an in vitro method for evaluating the therapeutic, prophylactic and/or diagnostic effect of a lung surfactant composition, which has dynamic swelling behaviour when dispersed in an electrolyte solution, the method comprising determining the half-life of the steady-state swelling and comparing the thus obtained half-life with in vivo-in vitro correlation curves in order to predict the therapeutic, prophylactic and/or diagnostic effect.

FIGURES

DETAILED DESCRIPTION

Figure 1:
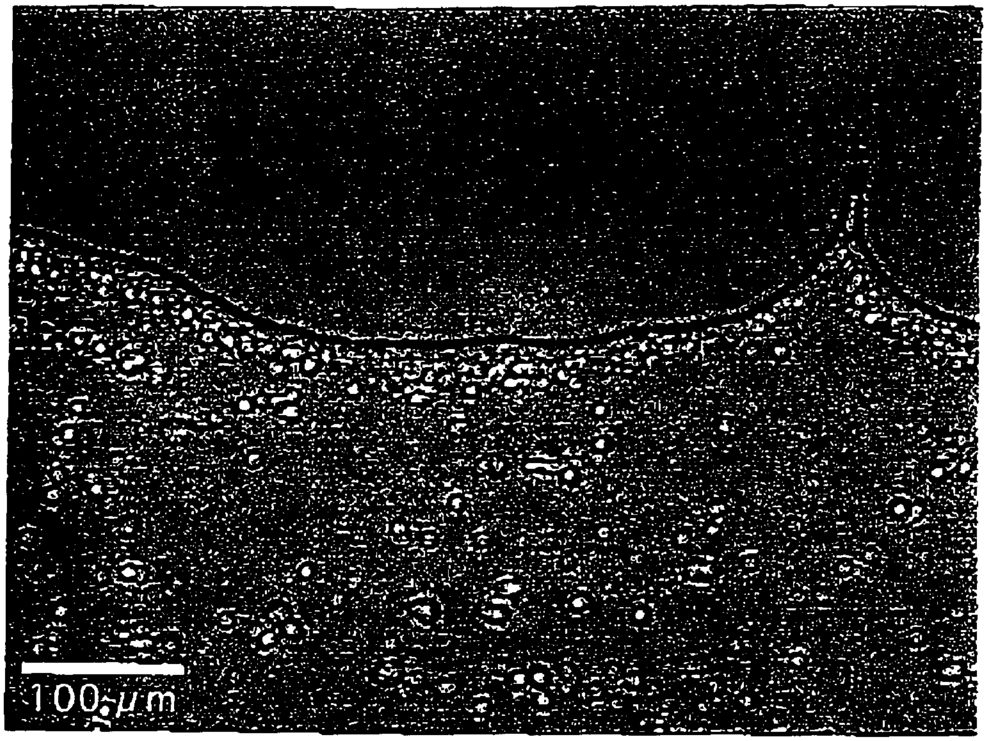
FIG. 1 shows a sample of 10% w/w PLS and 90% w/w Ringer solution viewed in the polarizing microscope 5 min after mixing. The PLS particles under swelling accumulate at the surface towards air.
Figure 2:
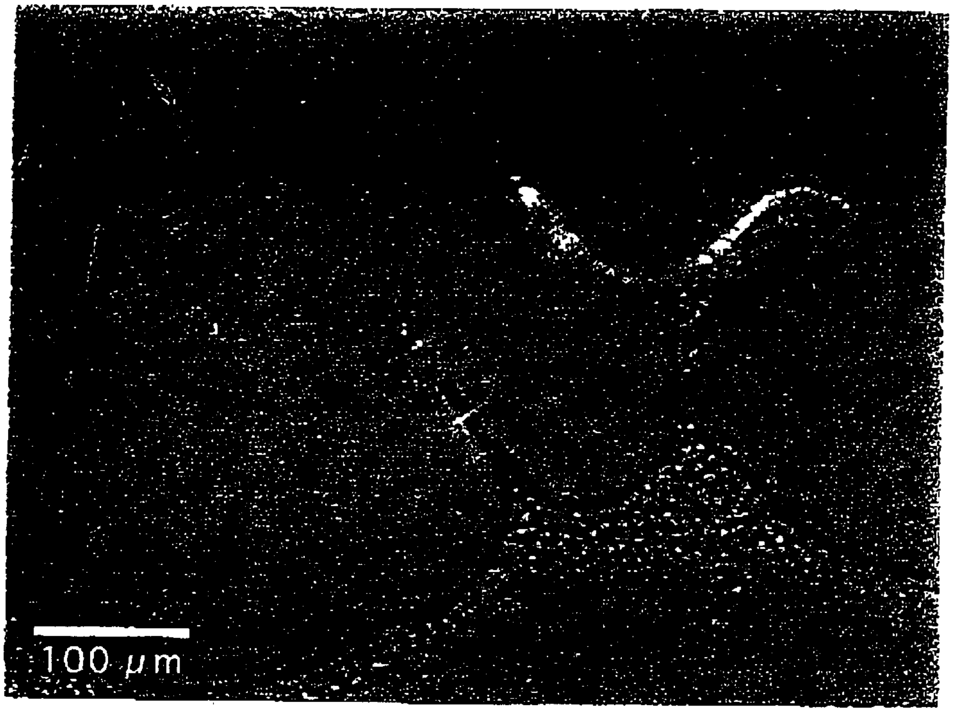
FIG. 2 show the sample as shown in FIG. 1 15 min after mixing. The "growing" tubules form branches as a treelike structure.
Figure 3:
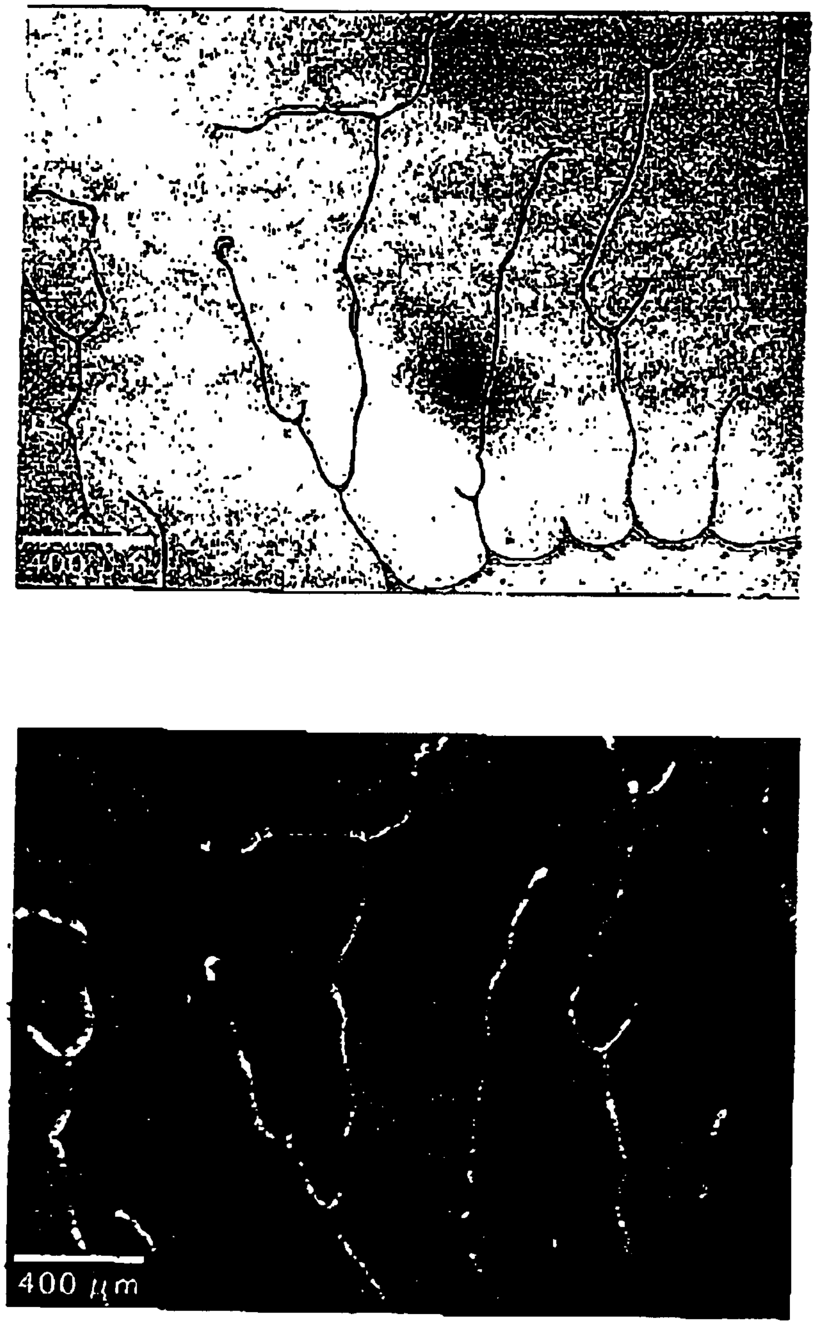
FIG. 3 shows the same sample as shown in FIG. 1 and FIG. 2 30 min after mixing. The photo above is taken in ordinary light whereas the photo below is taken in polarised light.
Figure 4:
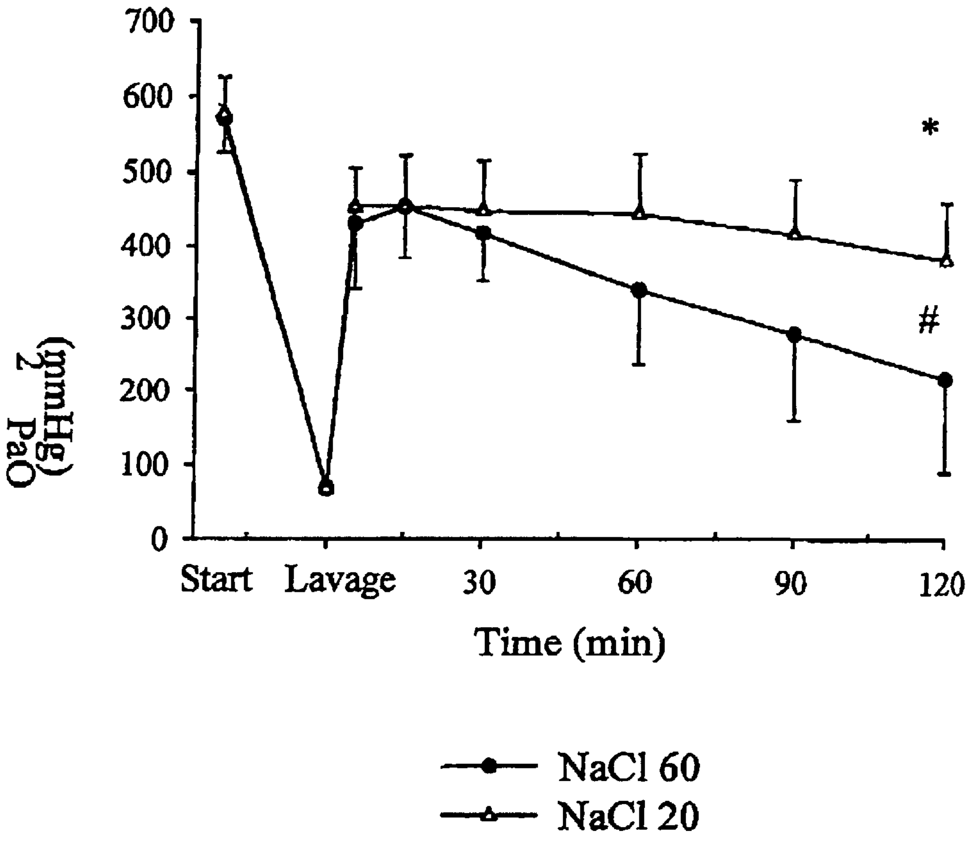
FIG. 4 shows the results from the animal studies described in Example 2 herein.

The present invention is based upon the surprising finding that an electrolyte containing medium, such as for example a Ringer solution or a sodium chloride solution, contrary to pure water, induces a highly dynamic swelling behaviour of a dispersion during the early stages of dispersing a lung surfactant in the medium. During this swelling period, a lipid-protein bilayer structure is organised towards an active establishment of an equilibrium conformation. This process involves spreading at an interface and can be followed in a polarizing microscope as formation of birefringent networks, which is illustrated in FIGS. 1–3 (described in further detail below). Birefringence is due to the occurrence of different refractive indices in different directions of the sample, and it indicates the occurrence of crystalline or liquid-crystalline order within the sample. Polar lipids like those in lung surfactant are known to form liquid-crystalline phases in water solutions. It is thus the optical character of these phases that can be followed by their birefringence.

Lung surfactant composition

Thus, the invention relates to a lung surfactant composition comprising a lung surfactant, which—when dispersed as powder or particles in 0.9% w/w sodium chloride in a concentration of 10% w/w at ambient and/or at body temperature—is capable of forming, in the course of swelling, a birefringent network or tubules at an air-liquid-solid interface within a time period of from about 0.5 to about 120 min such as, e.g., from about 3 to abut 60 min as observed by polarising microscopy. In contrast to a lung surfactant composition according to the present invention, known and marketed lung surfactant compositions do not possess such a dynamic swelling behaviour when dispersed in an electrolyte solution (see Example 4 herein).

The electrolyte-containing medium, in which the dynamic swelling occurs, is normally an aqueous medium containing one or more solvents or diluents. An excellent example of a solvent is water, which is preferred when the lung surfactant composition is administered to the lungs, but there may be situations where a small amount of other solvents such as, e.g., ethanol, isopropanol or polyethylene glycol can be present.

The dynamic changes that are observed are related to the presence of ions such as positive and/or negative ions, respectively. The electrolyte containing medium such as, e.g., an electrolyte solution may comprise at least one of the following cationic species: $Na^+$, $K^+$, $Li^+$, $Ca^{2+}$, $Mg^{2+}$ and/or $NH_4^+$ and/or at least one of the following anionic species: chloride, acetate, carbonate, hydrogen carbonate, dihydrogen phosphate ($H_2PO_4^-$), monohydrogen phosphate ($HPO_4^{2-}$), phosphate ($PO_4^{3-}$), tartrate, citrate, borate, fumarate, or the like. The electrolyte medium has normally such a constitution that it is physiologically acceptable, i.e. it does not harm or injury the body, especially not at the site of administration. In other words, the medium has normally a salt concentration and a pH, which corresponds to physiologically acceptable conditions. With respect to pH it means that the pH is in a range of from about 5 to about 8 and the salt concentration corresponds to that of a 0.9% sodium chloride solution or that of a Ringer or Ringer-acetate solution. The electrolyte solution may also be a 0.9% w/w sodium chloride solution, Ringer solution or Ringer-acetate solution.

A suitable electrolyte containing medium may also comprise one or more inorganic or organic salts, which impart ionic strength to the composition when dispersed in an aqueous medium such as, e.g., water. Suitable the inorganic salts for use in a lung surfactant composition according to the invention may be selected from the group consisting of alkaline metal salt such as, e.g., sodium chloride, potassium chloride, lithium chloride and alkaline earth metal salts such as, e.g. calcium chloride, magnesium chloride etc.

Examples of suitable organic salts for use according to the invention may be selected from the group consisting of acetates such as, e.g., sodium acetate, potassium acetate, lithium acetate, citrates, tartrates, fumarates, borates, phosphates, ammonium salt such as e.g. ammonium chloride etc.

The ionic strength of a suitable medium for use as a dispersion medium for a lung surfactant composition in order to obtain a dynamic swelling behaviour of the lung surfactant composition is also important. It is contemplated that the ionic strength should be at least about 5 mM such as, e.g., at least about 10 mM, at least about 15 mM, at least about 20 mM, at least about 25 mM, at least about 50 mM, at least about 75 mM, at least about 100 mM or at least about 125 mM. The ionic strength is calculated from the following equation:

$$I=0.5\Sigma c_1 z_1^2$$

wherein $c_1$ is the molar concentration of an individual ion in the medium and $z_1$ is the loading of the individual ion. Thus 0.9% w/w sodium chloride solution corresponds to an ionic strength of about 0.0156 M (15.6 mM) and Ringer-acetate solution has an ionic strength of about 0.138 M (138 mM).

The lung surfactant composition according to the invention may also comprise the ionic species or salts mentioned above. Especially in those cases where the lung surfactant composition is in the form of a powder or particles it could be appropriate to add a specific amount of the ionic species or salts so that the lung surfactant composition only should be dispersed in water in order to obtain the dynamic swelling behaviour.

The physiological relevance of the effects of the dynamic swelling behaviour of a lung surfactant composition according to the invention has further been tested in animal studies, showing significant clinical effects (see Example 2 herein).

To determine whether a lung surfactant has the ability of dynamic swelling and/or to determine the point in time at which the dynamic swelling phase is at its maximum and/or to determine an optimal point in time for administering a lung surfactant composition in accordance to the present invention, samples containing LS dispersed in a physiological electrolyte solution are prepared and samples of that mixture are regularly examined in a polarising microscope. Normally, the concentration of the lung surfactant should be from about 0.5 to about 45% w/w and the concentration of water should exceed about 55% w/w. Often the water content should be more than 80% w/w, such as about 90% w/w. At first, a homogeneous appearance will be obtained and the sample will be turbid with a viscosity like water. A view of the sample at this stage in the polarising microscope will resemble FIG. 1. Small particles with a weak birefringence surrounded by the electrolyte solution can be seen accumulated at the outer boundary of the liquid phase towards water. The birefringence will then be observed to increase followed by a remarkable increase of contact surface area of the liquid phase towards air. Tubular formations grow out from the front of the liquid and gradually branch out to form tree-like structures, which successively become birefringent, comparable to those shown in FIGS. 2 and 3. At approximately 60 min (range 0.5–120 min such as, e.g., 3–60 min) after adding the lung surfactant composition to the physiological electrolyte solution, a sample taken will not exhibit the dynamic swelling behaviour described above.

The term "birefringence" used herein means the separation of light, on passing through a crystal, into two unequally refracted, plane-polarized rays (of orthogonal polarizations). This effect occurs in crystals or liquid crystals in which the velocity of light is not the same in all directions; that is, the refractive index is anisotropic.

The term "network or tubules" refer to a remarkable increase of contact surface area of the liquid phase towards air resulting in tubules with branches which, when observed by polarising microscopy, become birefringent. The liquid surface may form a tree-like structure and the surface zone develops into a birefringent complex network (see FIG. 3).

It is contemplated that the time for maximum dynamic swelling varies with the concentration and nature of the components of a lung surfactant composition (e.g. mammalian extract or a semisynthetic or fully synthetic lung surfactant composition; even between batches of the same lung surfactant composition there may be variations), the method for its preparation and the composition of the dispersion medium employed (ionic strength, nature of the ionic species, concentration of the ionic species, pH etc), it is necessary to determine the dynamic swelling process and the point in time or time period for maximum dynamic swelling by a standardised procedure. Furthermore, the particle size of the lung surfactant composition is also important. Thus, it is contemplated that a reduction in particle size will lead to a faster dynamic swelling, i.e. the time to obtain steady state as well as the time to obtain maximum dynamic swelling will decrease. This feature may be used when it is desired to have a specific and well-defined time period for obtaining maximum dynamic swelling.

The lung surfactant used in the present invention are preferably derived from porcine lung, i.e. a porcine lung surfactant (PLS), but as the person skilled in the art will easily comprehend, they can as welt be derived from other mammalian origin, or even be synthetically produced. In one embodiment of the invention, the PLS is prepared from freshly slaughtered pigs. The pig lungs are minced and washed in saline solution and the mixture of proteins and lipids are then filtrated and centrifuged. Successively, the supernatant is centrifuged and the pellet of crude surfactant extracted as described (Bligh et al., 1959). The organic solvent phase is evaporated and neutral lipids removed by acetone. The preparation may finally be freeze-dried so that a lyophilised powder is obtained.

In one embodiment of the invention, the lung surfactant composition is obtained from porcine lungs (Leo Pharmaceutical Products, Ballerup, Denmark) but the surfactant can as well be obtained from alveolar cell cultures, or alternatively, be obtained chemically or synthetically e.g. by use of recombinant techniques.

Lung surfactant lipids and/or proteins can be obtained by culturing lung cells and harvesting the secreted lipids and/or proteins by methods well known to a person skilled in the art. Cell culture of lung surfactant is e.g. possible by use of the available ATCC cell line A549 (ATCC, 10801 University Boulevard, Manassas, Va. 20110-2209, USA), which is derived from a human adenocarcinoma of the lung. One embodiment of this invention therefore relates to the use of a lung surfactant derived from a cell line.

The extract described above contains hydrophobic proteins and phospholipids. It may further contain cholesterol, free fatty acids and fatty acid glycerides. In one embodiment of the invention, the lung surfactant composition may comprise surfactant proteins and lipids that are selected from a group consisting of phospholipids, DPPC, PG, fatty acids, SP-B and SP-C. In another embodiment of the invention, the lung surfactant composition may further comprise synthetic phospholipids and at least one of the hydrophobic proteins SP-B or SP-C. Said proteins may also be obtained as recombinant proteins.

Both SP-B and SP-C present in the LS extract used in the present invention are basic proteins under physiological pH-values, like those from nerve myelin. The lipids are both anionic, which can form electrostatic complexes with the cationic protein, and zwitterionic (PC).

As mentioned above, a lung surfactant composition according to the invention comprises phospholipids such as, e.g. saturated and unsaturated phospholipids or mixtures thereof. The concentration of phospholipids is from about 80 to about 99.5% w/w such as, e.g. from about 85 to about 98% w/w or from about 90 to about 98% w/w of the composition in dry form. The phospholipids may comprise dipalmityl phosphatidylcholine (DPPC). Furthermore, a lung surfactant composition according to the invention comprises surfactant proteins such as, e.g., SP-A, SP-B, SP-C and/or SP-D, preferably SP-B and/or SP-C. The total concentration of surfactant proteins is from about 0.5 to about 10% w/w, such as, e.g., from about 0.5% to about 7.5% w/w, from about 0.5 to about 5% w/w, from about 0.5 to about 2.5% w/w or from about 0.5% to about 2% w/w of the composition in dry form.

Before administration of a lung surfactant composition according to the present invention the lung surfactant composition may be dispersed in an aqueous electrolyte medium. This is performed by adding an electrolyte medium, for example Ringer solution, to a predetermined amount of lung surfactant composition, into a glass test tube. The dispersion is sucked up and ejected by a syringe repeatedly during about 0.5 min in order to facilitate mixing and interaction towards equilibrium. In a specific embodiment of the invention, Ringer-acetate from Pharmacia & Upjohn (Sweden) is used, which contains 130 mmol $Na^+$, 4 mmol $K^+$, 2 mmol $Ca^{2+}$, 1 mmol $Mg^{2+}$, 30 mmol $Ac^-$, and 100 mmol $Cl^-$. In another embodiment, said physiological electrolyte solution further comprises SP-A.

The microscopic observations of the dynamic swelling processes of a lung surfactant composition according to the present invention indicate that both the presence of ions and the presence of an air/solid/liquid interface is needed for the remarkable formation of a surface network textures as seen in FIGS. 2 and 3. This process represents a dynamically active state of a lung surfactant. Without being bound to any theory it is contemplated that extraction in an organic solvent and evaporation, as in the LS extract or preparation used in the present invention, means that polar regions are turned inside and hidden by hydrocarbon regions. The PG/SP-B and PG/SP-C ionic complexes are therefore assumed to change their conformations drastically in order to form bilayers, when exposed to water. This process takes some time. When ions from e.g., saline or Ringer solution are present, they may contribute to the dissociation of these complexes. This mechanism also explains why the network is not observed in lung surfactant samples swollen in distilled water.

Any reorganisation within the bilayer is to be expected to induce increased dynamics. This is probably the reason behind the elaborate birefringent network formation following the dispersion of LS powder or particles into Ringer solution. There seems to be a driving force at exposed interfaces to reduce the surface free energy, and the reorganisation process should favour the formation of low-energy interfaces towards solid surface, liquid and air. In embodiments of the present invention where it is suitable to employ a physiological electrolyte solution, the electrolyte solution is selected from the group consisting of saline (physiological sodium chloride) solution, Ringer and/or Ringer-acetate solution.

The unexpected physiological effects described above provide a new and improved means for the clinical use of lung surfactant compositions possessing a dynamic swelling behaviour. According to the present invention, the lung surfactant composition should thus be administered into the lungs together with a physiological electrolyte containing solution in a time-controlled fashion. Alternatively, the lung surfactant composition can be administered as a powder or as particles by means of e.g. a powder inhaler and then, the dynamic swelling process may occur in situ after application. If necessary, the administration may be supplemented by a subsequent administration of a suitable medium in the form of a neubulised liquid in order to enable a localised dynamic swelling behaviour of the lung surfactant composition. Use of powder inhalators may be especially useful when treating or preventing asthma, bronchitis or related respiratory conditions.

Thus, in other aspects the invention relates to the use of a lung surfactant composition according to the invention for the preparation of a medicament for the treatment or prevention of infant respiratory distress syndrome (IRDS), adult respiratory distress syndrome (ARDS), congenital diaphragmatic hernia, acute lung injury, patients treated with Extracorporeal Membrane Oxygenation and/or meconium aspiration pneumonia, or for the treatment or prevention of chronic obstructive lung disease, asthma, acute bronchitis, chronic bronchitis, bronchopulmonary dysplasia, lung infections, persistent pulmonary hypertension, lung hypoplasia, cancer, cystic fibrosis, alveolar proteinosis and/or congenital SP-B deficiency.

A suitable medicament may be prepared by dispersing the lung surfactant in powder or particulate form in a suitable dispersion medium, and the dispersing may be performed in a sufficient period of time to ensure dynamic swelling and formation of a network or tubules. A sufficient period of time is from about such as, e.g., from about 1 to about 100 min, from about 2 to about 90 min, from about 2 to about 80 min, from about 2 to about 70 min, from about 3 to about 60 min, from about 3 to about 50 min, from about 3 to about 45 min, from about 5 to about 40 min, from about 5 to about 35 min, from about 10 to about 35 min, from about 15 to about 35 min or from about 20 to about 35 min.

Pharmaceutical compositions and pharmaceutical kits

The present invention also relates to a pharmaceutical composition comprising a lung surfactant composition according to the invention. The pharmaceutical composition may be in solid (e.g. powder, particles, granules, sachets, tablets, capsules etc.), semi-solid (gels, pastes etc.) or liquid (solutions, dispersions, suspensions, emulsions, mixtures etc) form and adapted for administration via e.g. the respiratory organs. A pharmaceutical composition may thus be in powder or particulate form adapted to be dispersed in an aqueous medium before use.

A pharmaceutical composition in liquid form may be in the form of a dispersion comprising the lung surfactant composition and an electrolyte solution such as, e.g. a composition that is adapted to physiological conditions e.g. a physiologically acceptable solution.

A pharmaceutical composition according to the invention may further comprise another therapeutically, prophylactically and/or diagnostically active substance.

In another aspect, the invention relates to a pharmaceutical kit comprising a first and a second container, the first container comprising a lung surfactant composition according to the invention and the second container comprising a dispersion medium for the lung surfactant composition, accompanied by instructions for dispersing the lung surfactant composition in the dispersion medium before use.

The lung surfactant composition contained in the kit may be in powder or particulate form.

A pharmaceutical kit according to the invention may include instructions with recommendations for the time period during which the lung surfactant composition should be administered after dispersion in the dispersion medium.

The dispersion medium in a pharmaceutical kit according to the invention may be an electrolyte solution such as, e.g. a physiologically acceptable electrolyte solution such as, e.g. 0.9% w/w sodium chloride solution, Ringer solution or Ringer-acetate solution.

Furthermore, a pharmaceutical kit according to the invention may also comprise another therapeutically, prophylactically and/or diagnostically active substance.

In a specific embodiment the invention relates to a pharmaceutical kit comprising a first and a second container, the first container being in the form of an inhaler or the like comprising a pharmaceutical composition according to the invention, and the second container being in the form of a nebuliser or the like comprising an appropriate medium, which—when administered after administration of the pharmaceutical composition of the first container—ensures formation of a suitable in situ microenvironment for a dynamic swelling process.

For easy administration in clinical use, the present invention also encompasses a three component kit for time controlled administration of a lung surfactant composition, wherein a physiological electrolyte solution is achieved in the administered composition, containing a) a first component comprising a lung surfactant composition, b) a second component comprising a salt and, optionally, a dispersion medium, and c) a third component comprising a written instruction containing information about the period of time during which the aqueous swelling of lung surfactant composition takes place and how to use said kit.

As described above, the lung surfactant composition may contain varying mixtures of phospholipids and the proteins SP-B and/or SP-C. In a specific embodiment of the invention, the lung surfactant composition is dispersed in Ringer solution before administration.

The concentration of a lung surfactant composition in a pharmaceutical composition or in the ready to use pharmaceutical composition prepared from a kit is generally within the range of 0.5–300 mg/ml LS, such as at least 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, at least 100 mg/ml, at least 125 mg/ml, at least 150 mg/ml, at least 175 mg/ml or at least 200 mg/ml.

The pharmaceutical compositions and kits may be prepared by methods well known by a person skilled in the art.

Therapeutic, prophylactic and/or diagnostic use of a lung surfactant composition of the invention The present invention also relates to the use of a lung surfactant composition (which may contain a mixture of lipids and proteins from a lung extract, or a semisynthetic or even a fully synthetic lung surfactant, said mixture being dispersed in a electrolyte solution such as, e.g. a physiologic solution, for the preparation of a composition for administration at a predetermined time point or during a predetermined time period after adding said mixture comprising lipids and proteins to the electrolyte solution.

The present invention thus relates to the use of a lung surfactant composition wherein the lung surfactant is derived from a mammalian extract or from a semisynthetic or fully synthetic method, said composition being dispersed in an electrolyte solution, for the preparation of a composition for administration suitably at a predetermined point in time or during a predetermined time period, after adding said composition to said electrolyte solution, wherein said point of time or time period for administration has been determined microscopically as the half-time of the earliest time point at which the swelling behaviour of the dispersion has reached a steady-state. By administration into the alveoli at this time maximal use is made of the dynamic spreading during surfactant molecular reconformation in water, induced by an ionic interaction.

The present invention further relates to a method for determining and standardising the period of time during which the dynamic swelling of a lung surfactant takes place in an electrolyte medium, said method comprising adding the lung surfactant composition to the electrolyte medium and observing the dynamic swelling kinetics in a polarised microscope, as described above and in Example 1.

A lung surfactant composition according to the invention may be administered at any point in time to a patient in need thereof. Thus, the lung surfactant composition may be in the form of a dispersion in an electrolyte medium (such as, e.g. a physiological electrolyte solution) and it may then be administered at any appropriate time after the dispersion has been made As shown in Example 2 herein it is advantageous to utilize the dynamic swelling behaviour of a lung surfactant composition according to the invention in order to achieve an improved effect (i.e. the effect is larger or, alternatively, the dose may be reduced in order to achieve the same therapeutic effect).

In those cases where it is suitable to administer the lung surfactant composition at its maximum dynamic swelling, the time between mixing the lung surfactant in the form of a powder or particles (e.g. in lyophilised form or in dry form) in physiological electrolyte solution and the administration of said composition into the lungs for optimal effect is considered to be in the range of approximately 0.5–120 min such as, e.g., from about 1 to about 100 min, from about 2 to about 90 min, from about 2 to about 80 min, from about 2 to about 70 min, from about 3 to about 60 min, from about 3 to about 50 min, from about 3 to about 45 min, from about 5 to about 40 min, from about 5 to about 35 min, from about 10 to about 35 min, from about 15 to about 35 min or from about 20 to about 35 min. The present invention therefore also relates to the administration of a lung surfactant composition at a point in time that is at least 3 minutes and at most 60 minutes after adding said mixture comprising lung surfactant composition and proteins to said physiological electrolyte solution, such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 75, 90, 100 or 120 min after adding said mixture, or such as at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 75, 90, 100 or 120 min after adding said mixture. As described above, the optimal point in time for administering said composition will vary according to the quality of the dry powder and the choice of electrolyte solution that is used, and may even be longer than 60 minutes, such as between 60 and 75 minutes, or in certain cases even longer.

The time optimum can also vary somewhat between saline and Ringer solution. A good agreement between the biologically determined time optimum and the half-value of the time required to reach a steady-state birefringence front of the formulation as seen in the polarising microscope was found to exist in rat studies, and forms the basis of the present invention. From other studies with lung surfactant therapy of ARDS it is known that results from rats can be applied in human therapy. It is therefore concluded that the data derived from the rat studies are relevant also in humans. No such time effects at administration have been observed earlier.

The present invention also offers the possible use of the dynamic swelling behaviour of a lung surfactant composition for determining the quality of an LS composition. Access to an in vitro method to validate the quality is valuable and may replace time-consuming animal studies. Furthermore, the efficacy of the lung surfactant composition seems to be related to the performance quality as seen in the dynamic swelling behaviour.

The optimal concentration for lung administration of a lung surfactant composition in saline or Ringer solution is considered to be in the range between from about 4 to about 10% w/v. For use in the present invention, a concentration of 5% w/v is considered as suitable with regard to an administration through a tracheal tube and the limitation of administering too large volumes. A preferred embodiment of the invention thus relates to a composition that contains a lung surfactant, such as at least 4%, at least 5%, at least 6%, at least 7%, at least 8%, at least 9% or at least 10% w/v. A specific embodiment relates to a composition that contains at least 5% w/v lung surfactant.

One embodiment of the present invention relates to the use of a dynamic process of spreading of a lung surfactant composition comprising a lung surfactant for improved administration of said composition into the alveoli of a subject, characterised by administration of said lung surfactant composition suitably at a predetermined point in time or during a predetermined time period after adding the lung surfactant to an electrolyte medium such as, e.g. a physiological electrolyte solution. Said subject can be an animal including a human.

The dynamic swelling behaviour of a lung surfactant composition according to the invention imply that at a clinical use the lung surfactant composition should be administrated into the lungs together with a physiological electrolyte solution in a time-controlled fashion. Consequently, a method of treating a person in need thereof will comprise administering a lung surfactant composition dispersed (possibly reconstituted) in a physiological electrolyte solution, into the alveoli of said person during a predetermined span of time during which the dispersion is displaying an active dynamic spreading.

Such a method as described above can be used for the treatment, prevention or diagnosis infant respiratory distress syndrome (IRDS), adult respiratory distress syndrome (ARDS), congenital diaphragmatic hernia, acute lung injury, patients treated with Extracorporeal Membrane Oxygenation and/or meconium aspiration pneumonia, or for the treatment or prevention of chronic obstructive lung disease, asthma, acute bronchitis, chronic bronchitis, bronchopulmonary dysplasia, lung infections, persistent pulmonary hypertension, lung hypoplasia, cancer, cystic fibrosis, alveolar proteinosis and/or congenital SP-B deficiency.

In an especially preferred embodiment of the present invention, administration is performed via a tracheal tube into the lungs.

Pulmonary drug delivery

A lung surfactant composition, a pharmaceutical composition or a pharmaceutical kit according to the present invention may also be used as a carrier for other therapeutically, prophylactically and/or diagnostically active substance into body areas that are hard to access and thus provide an improved transport of substances e.g. over the alveolar wall Thus, the concept described herein can be used as a pulmonary drug delivery system for release (e.g. controlled release) of therapeutically, prophylactically and/or diagnostically active substance. Lung surfactants can serve as carriers or as vehicles for delivery of additional active substances such as, e.g. bronchodilators, anti inflammatory agents, histamine-receptor antagonists, inhalation steroids including corticosteroids, DNA-ases, immunotherapy including antibodies, vasodilators, antibiotics, growth factors, drugs enhancing epithelial integrity, factors accelerating lung maturation, mucous-dissolving agents including acetylcysteine, anti-neoplastic drugs, retinoids, vascular targeting compounds, anti-angiogenic substances, peptides, polypeptides, proteins and/or gene-therapy including viral vectors and naked DNA. These potential uses of a lung surfactant composition for pulmonary drug delivery would be applicable in particular in the following diseases: chronic obstructive lung disease, asthma, bronchopulmonary dysplasia, lung infections, persistent pulmonary hypertension, lung infections, lung hypoplasia, bronchopulmonary dysplasia (retinoids including Vitamin A), respiratory distress syndrome, cancer, cystic fibrosis, alveolar proteinosis, and/or congenital SP-B deficiency.

Alternatively, the drug delivery system provided by the present invention can of course be as applicable for delivering drugs into a subject in need thereof, even if said subject does not suffer from a lung-related disease or a disease related to lung sufficiency. Such disease could for illustrative purposes only and not limited to, for example be either cancer and/or diabetes.

In those cases where a lung surfactant composition according to the invention is used as a carrier for delivery an active substance to the respiratory organs, the time period in which the dynamic swelling of the lung surfactant composition may deliberately be changed (e.g. by change in particle size, concentration of the lung surfactant composition, concentration of the electrolytes, nature of the ionic species involved etc.) in order to obtain e.g. modified delivery of the active substance to the subject. The modified release may be a release that is extended over a predetermined period of time (it can be from about 4 hours to about 3–5 days).

Another possible field of use for the present invention is the treatment of patients after surgery, wherein the composition is applied in order to prevent or avoid adhesion between tissues in mutual contacts.

The field of pulmonary drug delivery is very active at present. The main delivery route is the oral delivery route, where many complications have been reported, which do not exist in pulmonary delivery, such as e.g. degradation of the drugs by the low pH or any of the enzymes in the gastrointestinal tract. The physiological nature of the surfactant makes it ideal as a vehicle in delivery into the lungs of almost any drug used systemically.

Additionally, therapeutic agents based on the present invention may comprise a pharmaceutical substance encapsulated in surfactant liposomes.

The invention is further illustrated in the following non-limiting examples.

EXAMPLES

Example 1

Compositions of porcine lung surfactant (PLS) and their swelling behaviour—In vitro observation of a dynamic swelling process Preparation of a PLS composition All experiments were performed with a porcine lung surfactant extract (Leo Pharmaceutical Products, Ballerup, Denmark) (PLS) prepared from freshly slaughtered pigs. PLS was extracted from minced porcine lungs according to a method of Bligh and Dyer (Can. J. Biochem. Physiolol. 1959, 37, 911–917). The organic solvent phase was evaporated and neutral lipids were removed by acetone. The preparation obtained was finally freeze-dried. The product was obtained as a powder composition that was composed of a mixture of saturated and unsaturated phospholipids (90–98% w/w of the powder composition), surfactant proteins SP-B and SP-C (0.5–2.0% w/w) and other lipids (up to 10% w/w). The composition was used in the following experiments.

Preparation of aqueous samples of PLS

Aqueous samples of porcine lung surfactant (Leo Pharmaceutical Products, Ballerup, Denmark) (PLS) were prepared by adding PLS to water or varying proportions saline solution or Ringer solution in glass test tubes. The concentration of PLS in the electrolyte solution employed was in all experiments 10% w/w, whereas concentration of the electrolytes in the electrolyte solution was varied (e.g. 0.9% w/w or a 1.8% w/w sodium chloride solution. The dispersion was sucked up and ejected by a syringe repeatedly during about 0.5 min to achieve mixing, In a first experiment Ringer-acetate from Pharmacia & Upjohn was used as a solvent ($Na^+$ 130 mmol, $W^+$ 4 mmol, $Ca^{2+}$ 2 mmol, $Mg^{2+}$ 1 mmol, $Ac^-$ 30 mmol, $Cl^-$ 100 mmol). A droplet of equilibrated or freshly prepared samples was transferred to microscope slides for examination either during swelling of the dry PLS powder or after equilibrium had been reached. A coverslip was put down on the droplet very gently, in order to avoid air bubble incorporation.

Observations in a microscope were performed at 25° C. and/or at 42° C. A Leitz polarising microscope was used equipped with a Sony CD camera and colour printer.

In the polarising microscope the swelling behaviour of a sample containing 10% (w/w) PLS and 90% Ringer solution was studied. At different time points samples were taken from the bulk solution and put on microscopy slides with coverslips. After about 5 min a homogenous appearance was obtained, the sample was turbid, and particles with a weak birefringence surrounded by the Ringer solution accumulated at the outer boundary of the liquid phase (FIG. 1). A remarkable increase of contact surface area of the liquid phase towards air was seen. Tubular formations were seen at the front of the liquid. The "growing" tubules formed branches, which successively became birefringent, as shown in FIG. 2 recorded at about 15 minutes after sample mixing. FIG. 3 (above and below) shows a surface view after about 30 min in both ordinary light (above) and polarized light (below). The surface zone had developed into a birefringent complex network. This branching behaviour ended after approximately 40–60 min, with some variation from one batch to the other.

When PLS was swollen in physiological saline solution there was a similar growth of networks at the interface. Two different concentrations of sodium chloride were employed, 0.9% w/w and 1.8% w/w, respectively. Irrespective of the sodium concentration employed, a network structure like the one seen in FIG. 3 was observed.

This dynamic behaviour with pronounced surface enlargement towards birefringent network formation was only observed when PLS was swollen in saline or Ringer solution, not with water. Also, when the water was made isotonic by the addition of glycerol, PLS swollen in this solution still lacked the dynamic swelling behaviour shown by the electrolyte solutions.

Further experiments have confirmed that PLS will only form a birefringent network or tubule structure if a certain minimum concentration of electrolytes is present in the dispersion medium. In other words, the formation of a birefringent network or tubule structure is dependent on the electrolyte concentration and/or the ion strength of the dispersion medium.

As mentioned above some of the experiments were performed at two different temperatures. The dynamic swelling behaviour leading to the formation of a birefringent network or tubule structure was seen at both temperatures.

Example 2

Animal experiments—in vivo behaviour of PLS compositions with different degrees of swelling Animal protocol The protocol was approved by the local Animal Committee of Erasmus University, Rotterdam; care and handling of the animals were in accordance with the NIH guidelines Sixteen male Sprague-Dawley rats (Harlan, CPH, Zeist, the Netherlands) bodyweight (BW) 240–320 g were anesthetized with nitrous oxide, oxygen and isoflurane (65/33/2%), tracheotomized and a catheter was inserted into a carotid artery. Anaesthesia was maintained with pentobarbital sodium (Nembutal; Algin BV, Maaassluis, the Netherlands) 60 mg/kg/h i.p. injections; neuromuscular block was produced with pancuronium bromide (Pavulon; Organon Technika, Boxtel, the Netherlands) 2.0 mg/kg/h i.m. Body temperature was kept within normal range by mean of a heating pad.

Rats were connected to a ventilator (Servo Ventilator 300, Siemens-Elema, Solna, Sweden) and ventilated with pure oxygen in a pressure-controlled mode, frequency 30 bpm, an I/E ratio of 1:2, a peak airway pressure (PIP) of 12 cm $H_2O$ and a positive end-expiratory pressure (PEEP) of 2 cm $H_2O$. Initially, PIP was increased to 20 cm $H_2O$ for 1 min to recruit atelectatic areas. Next, surfactant deficiency was induced by repeated whole-lung lavage (BAL) to achieve a $PaO_2$<85 mm Hg. Just before the first lavage, PIP and PEEP were elevated to 26 and 6 cm $H_2O$, respectively Treatment was: exogenous surfactant (35 mg/kg bodyweight dispersed in saline 0.9% w/w 25 mg/ml). The PLS saline mixture was repeatedly drawn in and out of a syringe during 0.5 min. The time of swelling dynamic maximum (corresponding to $t_{1/2}$) for the PLS batch used was established to be 20 min. One group of eight rats received surfactant 20 min after preparation of the surfactant composition and the other group of eight rats received surfactant 60 min after the preparation of the surfactant composition. Surfactant composition (4 ml/kg BW±0.4 ml) was administered directly into the endotracheal tube followed by a bolus of air (14 ml/kg) (ventilator settings not changed).

Blood samples for measurements of $PaO_2$ and $PaCO_2$ were taken from the carotid artery before BAL and 5 min after the last lavage (directly followed by treatment) and at the following times 5, 15, 30, 60, 90 and 120 min after surfactant administration (ABL 505, Radiometer A/S, Copenhagen, Denmark).

After the experiments, the animals were killed with an overdose of pentobarbital sodium.

Statistical analysis

Statistical analysis was performed using SPSS 10.0 statistical software package (SPSS Inc. Chicago, Ill.). Intergroup comparisons were analysed with ANOVA. Intragroup comparisons were analysed with repeated measures of ANOVA. If ANOVA resulted in $p<0.05$ a Tukey post-hoc test was performed. Statistical significance was accepted at $p<0.05$.

Results

As discussed above, after 40 min the PLS saline solution samples had reached a steady state of swelling and at about half-time of this process (i.e. at about 20 min) there is a maximum in the dynamics involved in network formation. Two time windows were therefore chosen (20 and 60 min after mixing with saline) to observe whether the in vitro interfacial dynamics correlated with in vivo surfactant function.

To optimise the detection of any effect of the swelling behaviour on the surfactant function in vivo, a low dose of PLS was used. The low dose was by itself not sufficient to completely restore the induced lung injury, as shown by the $PaO_2$ data discussed below.

FIG. 10 shows the $PaO_2$ levels over time in both groups, which received PLS, dispersed either 20 min or 60 min before administration. After PLS administration $PaO_2$ improved in both groups, but never reached pre-lavage during the 120 min study period. There was no difference in the $PaO_2$ levels at 5 min after administration and at the end of the experiment (120 min). However, $PaO_2$ dropped significantly from 5 to 120 min after PLS instillation ($p<0.001$) in the group in which PLS was mixed 60 min before administration. Furthermore, the difference in $PaO_2$ between the two groups at 120 min was also significant ($p<0.01$).

The conclusion is that surfactant function represented by arterial oxygenation of the maximum swelling condition is superior to the steady state PLS condition. A possible explanation for the better effect of surfactant replacement during the dynamic swelling phase is that the dynamic swelling provides a better distribution of the instilled surfactant. The tree-like projections seen when dynamic swelling is examined in in vitro conditions extend over millimeters, i.e., over several alveolar diameters.

Very important results of this study are demonstration of a variation of the physiological effect at administration in relation to the aqueous mixing time, a time which seems to be directly related to the dynamics of swelling observed in vitro. This means that lung surfactant extract compositions should be analysed with regard to the swelling dynamics in order to determine the maximum in dynamics. In general this time is found to be about the half time of achievement of steady state. This pre-determined time, which may vary from one production batch of PLS to another, could enhance the therapeutic effect after administration.

A few additional rat experiments were done using Ringer solution instead of saline solution, and they showed the same improvements in oxygenation at administration during the maximum in swelling dynamics compared to administration when the swelling dynamics had stopped.

When just water with glycerol was used in the PLS composition the therapeutic effect after administration was dramatically reduced compared to the electrolyte containing solutions.

Example 3

Dynamic swelling behaviour of PLS as a parameter for quality control analysis

The aim of the present study is to develop a suitable in vitro test method to determine whether a specific batch of PLS (or any other lung surfactant possessing a dynamic swelling behaviour as described herein) fulfils predetermined requirements in order to be suitable for therapeutic, prophylactic and/or diagnostic use. Normally, such a test is performed in animal studies such as those described in Example 2, but such tests are expensive and involve the use of test animals. Generally, there is a desire to substitute tests involving test animals with in vitro tests, if possible. The results shown in Example 1 and 2 indicate that an in vivo—in vitro correlation can be established between the therapeutic effect in vivo and the time for maximum dynamic swelling.

The establishment of such an in vivo—in vitro correlation is typically performed based on results from at least 10 different batches of PLS. In the following is described a procedure for determining an in vivo—in vitro correlation.

Samples of different batches of PLS prepared as described in Example 1 are subjected to the procedure described in Example 1 to investigate the dynamic swelling behaviour of PLS in dispersion. 10% w/W PLS in powder or particulate form is dispersed in 90% w/w of a 0.9% w/w sodium chloride solution. Samples of the PLS dispersion are observed in a polarising microscope as described in Example 1, and the time at which birefringent tubule, branching or network formation occurs in each sample is noted as is the time when the swelling reaches a steady state. Also, the degree of interfacial length increases, and the strength of birefringence may be recorded. Based on the microscopy observations, a maximum dynamic swelling is set for each sample at about half the time required to reach steady state swelling Also, the quality of the dynamic swelling behaviour may be classified.

Samples of each PLS dispersion tested microscopically are also tested in the animal model described in Example 2 to establish a correlation between in vitro swelling dynamics and in vivo surfactant function. PLS samples are instilled in the animals at different points in time after preparation of each dispersion, and the effect of PLS instillation is determined by measuring the PaO2 level according to the method of Example 2. The intervals between the time at which the PLS dispersion is prepared and the time at which it is instilled in the animal resulting in a pronounced improvement in $PaO_2$ levels are noted.

Based on comparisons of said intervals and the time periods observed to give rise to maximum dynamic swelling in vitro, a correlation between in vitro behaviour and in vivo effect may be established with a view to defining time periods during which dynamic swelling of PLS dispersions give rise to an optimum surfactant effect. Also, the quality of the dynamic swelling behaviour may be taken into account.

Once defined for a representative number of samples, such time periods may then be used as standards for validation and/or quality control of subsequently produced batches of PLS. The in vivo—in vitro relationship (correlation) can be used in the validation of individual batches of PLS instead of using time-consuming animal experiments and certain limits can be set for the point of time at which the maximum dynamic swelling occurs if the batch is acceptable. The limits are typically set at $t_{1/2}$±15%, $t_{1/2}$±10%, $t_{1/2}$±7.5% or $t_{1/2}$±5%. This implies that samples of PLS batches are subjected to the in vitro testing procedure outlined above, and batches exhibiting a desired dynamic swelling behaviour characterised by formation of birefringent tubules or networks within a predetermined standard period of time are accepted, while batches not exhibiting this behaviour are discarded.

Based on data obtained so far with PLS dispersions, it would appear that periods of time within which PLS dispersions may advantageously be administered are in the range of about 15–30 minutes from dispersing the PLS powder in saline.

Example 4

Swelling behaviour of marketed lung surfactant compositions

Various marketed lung surfactant compositions have been tested with respect to their swelling behaviour. The following products were tested: Alveofact, Curosurf and Exosurf. Alveofact and Exosurf are in the form of dry powders whereas Curosurf is in the form of a dispersion. Table 1 below gives a summary of commercially available lung surfactant preparations.

TABLE 1

Commercially available surfactant preparations (from D. Gommers. Thesis 1998, University of Rotterdam, "Factors affecting surfactant responsiveness"

| Preparation | Producer | Composition | Phospho-Lipids* | Proteins | Clinical doses (mg/kg) |
|---|---|---|---|---|---|
| Alec ™ ( = Pumactant) | Britannia, Redhill, England | Synth. DPPC and PG (7:3) | 100% | 0% | 100 |

TABLE 1-continued

Commercially available surfactant preparations (from D. Gommers. Thesis 1998, University of Rotterdam, "Factors affecting surfactant responsiveness"

| Preparation | Producer | Composition | Phospho-Lipids* | Proteins | Clinical doses (mg/kg) |
|---|---|---|---|---|---|
| Alveofact* ( = SF-RI 1) | Thomae, Biberach, Germany | Lipid extract from bovine lung lavage | 88% | 1% | 100 |
| BLES | F. Possmayer, Univ. Western, Ontario, USA | Lipid extract from calf lung lavage | 90% | 1% | 100 |
| Curosurf*# | Chiesi, Parma, Italy | Lipid extract from minced porcine lungs | 99% | 1% | 200 |
| Exosurf* | Burroughs-Wellcome, New York, USA | Synth. DPPC, hexadecanol, tyloxapol | 84% | 0% | 67.5 |
| Infasurf* ( = CLSE) | Ony Inc., New York, USA | Lipid extract from calf lung lavage | 95% | 1% | 100 |
| Surfacten* ( = surfactant-TA) | Tokyo Tanabo, Tokyo, Japan | Lipid extract from minced bovine lungs + synth. DPPC | 84% | 1% | 100 |
| Survanta ™ ( = Beractant) | Abbott, Wiesbaden, Germany | Lipid extract from minced bovine lungs + synth. DPPC | 84% | 1% | 100 |

DPPC, dipalmitoylphosphatidylcholine. PG, phosphatidylglycerol. Synth., synthetic. *, by weight.

Most of the lung surfactants employed are extracts from calf or bovine lungs. However, Curosurf contains an extract from minced porcine lungs with a relatively high content of phospholipids (99% w/w).

The swelling behaviour was determined by dispersing 50 mg of lung surfactant in 1000 mg 0.9% w/w sodium chloride as described in Example 1, and the dispersions were observed in a polarisation microscope.

All products except Curosurf are in the form of powders. Curosurf is in the form of a suspension and the swelling behaviour of Curosurf was determined by putting a droplet on a slide with a coverslip.

All products swelled after dispersion in saline. However, none of the products investigated in this example exhibited a dynamic swelling behaviour with formation of a birefringent network, i.e. the products do not swell dynamically as seen with the PLS.

What is claimed is:

1. An isolated lung surfactant composition comprising a lung surfactant, which-when dispersed as powder or particles in 0.9% w/w sodium chloride in a concentration of 10% w/w at ambient temperature-is capable of forming, in the course of swelling, a birefringent network or tubules at an air-liquid-solid interface within a time period of from about 0.5 mm to about 120 minutes as observed by polarising microscopy.

2. A method according to claim 1, wherein the lung surfactant composition is administered as a medicament prepared by dispersing the lung surfactant in powder or particulate form in a suitable dispersion medium.

3. A method according to claim 1, wherein the lung surfactant composition is administered as a medicament prepared by dispersing the lung surfactant in powder or particulate form in a suitable dispersion medium.

4. A method according to claim 3, wherein the mammal is a human.

5. A method according to claim 3, wherein dispersing is performed for a sufficient period of time to ensure dynamic swelling and formation of a birefringent network or tubules.

6. A method according to claim 3, wherein the lung surfactant composition is administered as a medicament prepared by dispersing the lung surfactant in powder or particulate form in a suitable dispersion medium.

7. A method according to claim 6, wherein the sufficient period of time is from about 0.5 to about 120 minutes.

8. A method according to claim 6, wherein the sufficient period of time is from about 1 to about 90 minutes.

9. A method according to claim 6, wherein the sufficient period of time is from about 2 to about 70 minutes.

10. A method according to claim 6, wherein the sufficient period of time is from about 3 to about 45 minutes.

11. An isolated lung surfactant composition, which-when dispersed as a powder or as particles in an electrolyte solution having an ionic strength of at least about 5 mM or at an ionic strength corresponding to physiological conditions, and the thus obtained dispersion has a concentration of water of at least about 55% w/w,- is subject to a dynamic swelling process during which a birefringent network or tubules are formed, as observed by polarising microscopy, and the dynamic swelling process ends when steady-state is reached.

12. A lung surfactant composition according to claim 11, wherein the electrolyte solution has an ionic strength of at least about 10 mM.

13. A lung surfactant composition according to claim 11, wherein the dispersion obtained has a concentration of water of at least about 60% w/w.

14. A lung surfactant composition according to claim 11, wherein the lung surfactant-when dispersed in an electrolyte solution-is in the form of a liquid crystalline lamellar phase.

15. A lung surfactant composition according to claim 11, wherein the electrolyte solution comprises at least one of the following cationic species: Na+, K+, U+, Ca2−, Mg2+ and/or NH4+.

16. A lung surfactant composition according to claim 11, wherein the electrolyte solution comprises at least one of the following anionic species selected from the group consisting of: chloride, acetate, carbonate, hydrogen carbonate, dihydrogen phosphate ($H_2PO_4$), monohydrogen phosphate ($HPO_4^{2-}$), phosphate ($PO_4^{3-}$), tartrate, citrate, borate and furnarate.

17. A lung surfactant composition according to claim 11, wherein the dispersion obtained has a concentration of water of at least about 70% w/w.

18. A lung surfactant composition according to claim 11, wherein the dispersion obtained has a concentration of water of at least about 80% w/w.

19. A lung surfactant composition according to claim 11, wherein the dispersion obtained has a concentration of water of at least about 90% w/w.

20. A lung surfactant composition according to claim 11, wherein the electrolyte solution is a sodium chloride solution.

21. A lung surfactant composition according to claim 20, wherein the electrolyte solution is a sodium chloride solution selected from the group consisting of: a 0.9% w/w sodium chloride solution, Ringer solution and Ringer-acetate solution.

22. A lung surfactant composition according to claim 1 or 11 comprising dipalmitylphosphatidylcholine (DPPC).

23. A lung surfactant composition according to claim 1 or 11 comprising at the most up to 10% w/w of other lipids than phospholipids.

24. A lung surfactant composition according to claim 1 or 11, wherein the lung surfactant comprises synthetic components.

25. A lung surfactant composition according to claim 1 or 11, wherein the lung surfactant is obtained from mammalian alveolar cell cultures.

26. A lung surfactant composition according to claim 1 or 11 further comprising another therapeutically, prophylactically and/or diagnostically active substance.

27. A method for preventing adhesion between tissues in mutual contact comprising application of a lung surfactant composition according to claim 1 or 11.

28. A lung surfactant composition according to claim 1 or 11, wherein the lung surfactant is obtained from a mammalian lung.

29. A lung surfactant composition according to claim 28, wherein the lung surfactant is extracted from the mammalian lung.

30. A lung surfactant composition according to claim 28, wherein the mammalian lung is cattle, bovine, porcine, monkey or human lung.

31. A method for the preparation of a pharmaceutical composition, the preparation comprising dispersing a lung surfactant composition according to claim 1 or 11 until a birefringent network or tubules are formed at an air-liquid-solid interface as observed by polarisation microscopy.

32. A method according to claim 31, wherein dynamic swelling of the lung surfactant occurs within a time period of from about 0.5 to about 120 minutes.

33. A method according to claim 31 wherein the composition is dried.

34. A lung surfactant composition according to claim 1 or 11, wherein the lung surfactant comprises phospholipids.

35. A lung surfactant composition according to claim 34, wherein the phospholipids are present in the form of a mixture of saturated and unsaturated phospholipids.

36. A lung surfactant composition according to claim 34, wherein the concentration of phospholipids is from about 80 to about 99.5% w/w of the composition in dry form.

37. A lung surfactant composition according to claim 34, wherein the concentration of phospholipids is from about 85 to about 98% w/w of the composition in dry form.

38. A lung surfactant composition according to claim 34, wherein the concentration of phospholipids is from about 90 to about 98% w/w of the composition in dry form.

39. A lung surfactant composition according to claim 1 or 11 comprising surfactant proteins.

40. A lung surfactant composition according to claim 39, wherein the surfactant proteins are SP-B and/or SP-C.

41. A lung surfactant composition according to claim 39, wherein the total concentration of surfactant proteins is from about 0.5 to about 10% w/w of the composition in dry form.

42. A lung surfactant composition according to claim 39, wherein the surfactant protein is a recombinant protein.

43. A lung surfactant composition according to claim 39 comprising surfactant proteins selected from the group consisting of SP-A, SP-B, SP-C and combinations thereof.

44. A lung surfactant composition according to claim 39, wherein the total concentration of surfactant proteins is from about 0.5 to about 5% w/w of the composition in dry form.

45. A method for the treatment and/or prevention of a lung disease or condition in a mammal, the method comprising administering to the mammal in need thereof an effective amount of a lung surfactant composition according to claim 1 or 11.

46. A method according to claim 45, wherein the administration takes place during a dynamic swelling phase of the lung surfactant composition.

47. A method according to claim 45, wherein the lung disease or condition is selected from the group consisting of infant respiratory distress syndrome (IRDS), adult respiratory distress syndrome (ARDS), congenital diaphragmatic hernia, acute lung injury, patients treated with Extracorporeal Membrane Oxygenation and meconium aspiration pneumonia.

48. A method according to claim 45, wherein the lung disease or condition is selected from the group consisting of chronic obstructive lung disease, asthma, acute bronchitis, chronic bronchitis, bronchopulmonary dysplasia, lung infections, persistent pulmonary hypertension, lung hypoplasia, cancer, cystic fibrosis, alveolar proteinosis and congenital SP-B deficiency.

49. A pulmonary drug delivery system comprising a lung surfactant composition according to claim 1 or 11.

50. A pulmonary drug delivery system according to claim 49, wherein the system further comprises another therapeutically, prophylactically and/or diagnostically active substance.

51. A pulmonary drug delivery system according to claim 50, wherein the therapeutically, prophylactically and/or diagnostically active substance comprises peptides, polypeptides or proteins.

52. A lung surfactant composition according to claim 1 or 11 further comprising one or more inorganic or organic salts, which impart ionic strength to the composition when dispersed in an aqueous medium.

53. A lung surfactant composition according to claim 52, wherein the aqueous medium is water.

54. A lung surfactant composition according to claim 52, wherein the one or more inorganic salts comprises an alkaline earth metal salt.

55. A lung surfactant composition according to claim 54, wherein the alkaline earth metal salt is selected from the group consisting of sodium chloride, potassium chloride, lithium chloride and alkaline earth metal salts.

56. A lung surfactant composition according to claim 52, wherein the one or more organic salts comprises an acetate.

57. A lung surfactant composition according to claim 56, wherein the acetate is selected from the group consisting of sodium acetate, potassium acetate, lithium acetate, citrates, tartrate, fumarate, borate, and phosphate.

58. A lung surfactant composition according to claim 56, wherein the ammonium salt comprises ammonium chloride.

59. A pharmaceutical composition comprising a lung surfactant composition according to claim 1 or 11.

60. A pharmaceutical composition according to claim 59 in powder or particulate form adapted to be dispersed in an aqueous medium.

61. A pharmaceutical composition according to claim 59, wherein the composition is adapted to physiological conditions.

62. A pharmaceutical composition according to claim 59 further comprising another therapeutically, prophylactically and/or diagnostically active substance.

63. A pharmaceutical kit comprising a first and a second container, the first container being in the form of an inhaler or the like comprising a pharmaceutical composition according to claim 8, and the second container being in the form of a nebuliser comprising an appropriate medium, which—when administered after administration of the pharmaceutical composition of the first container—ensures formation of a suitable in situ microenvironment for a dynamic swelling process.

64. A pharmaceutical composition according to claim in the form of a powder or particles adapted to be administered from an inhaler.

65. A pharmaceutical composition according to claim 64, wherein the mean particle size and/or the electrostatic properties of the powder or particles have been adjusted to conditions required in order to reach specific sites in the respiratory organs after administration via an inhaler.

66. A pharmaceutical composition according to claim 59 in liquid form.

67. A pharmaceutical composition according to claim 66, wherein the liquid is in the form of a dispersion comprising the lung surfactant composition and an electrolyte solution.

68. A pharmaceutical composition according to claim 67, wherein the electrolyte solution is a physiologically acceptable solution.

69. A pharmaceutical kit comprising a first and a second container, the first container comprising a lung surfactant composition according to claim 1 or 11 and the second container comprising a dispersion medium for the lung surfactant composition, accompanied by instructions for dispersing the lung surfactant composition in the dispersion medium.

70. A pharmaceutical kit according to claim 69, wherein the lung surfactant composition is in powder or particulate form.

71. A pharmaceutical kit according to claim 69, wherein the instructions include recommendations for the time period during which the lung surfactant composition should be administered after dispersion in the dispersion medium.

72. A pharmaceutical kit according to claim 69 further comprising another therapeutically, prophylactically and/or diagnostically active substance.

73. A pharmaceutical kit according to claim 69, wherein the dispersion medium is an electrolyte solution.

74. A pharmaceutical kit according to claim 73, wherein the electrolyte solution is a physiologically acceptable electrolyte solution selected from the group consisting of 0.9% w/w sodium chloride solution, Ringer solution and Ringer-acetate solution.

* * * * *